United States Patent [19]

Byers et al.

[11] Patent Number: 5,223,542
[45] Date of Patent: Jun. 29, 1993

[54] METHOD FOR INHIBITING SPRUCE BARK BEETLES

[76] Inventors: John Byers, 125 Everett St., Lakewood, Colo. 80226; Jan Löfquist, Vallby 16, S-245 00 Staffanstorp, Sweden

[21] Appl. No.: 741,530

[22] PCT Filed: Feb. 6, 1990

[86] PCT No.: PCT/SE90/00074
§ 371 Date: Sep. 10, 1991
§ 102(e) Date: Sep. 10, 1991

[87] PCT Pub. No.: WO90/09104
PCT Pub. Date: Aug. 23, 1990

[30] Foreign Application Priority Data

Feb. 9, 1989 [SE] Sweden ............................. 8900442

[51] Int. Cl.$^5$ ............................................. A01N 35/06
[52] U.S. Cl. ..................................... 514/691; 514/919; 424/DIG. 10
[58] Field of Search .................. 514/691, 919; 424/84, 424/DIG. 10

[56] References Cited

U.S. PATENT DOCUMENTS

| | | | |
|---|---|---|---|
| 4,325,941 | 4/1982 | Dal Moro et al. | 424/84 |
| 4,839,383 | 6/1989 | Vité | 514/691 |
| 5,035,886 | 7/1991 | Chakrabarti et al. | 424/84 |

OTHER PUBLICATIONS

Bakke, Alf, "Inhibition of the Response in IPS Typographus . . . ", Z. Angew Entomol. 92(2), 1981, pp. 172–177.

Heuer et al., "Chalcogran: Unique Kairomone-governed Predator-prey Relations Among Ostomid and Scolytid Beetles". Naturwissenschaften vol. 71 (4), 1984, pp. 214–215.

Primary Examiner—Richard L. Raymond
Assistant Examiner—John D. Pak
Attorney, Agent, or Firm—Burns, Doane, Swecker & Mathis

[57] ABSTRACT

The present invention relates to a method for inhibiting the six toothed spruce bark beetle *Pityogenes chalcographus*, by preventing aggregation and/or infestation of spruce, whereby one applies an inhibitory active amount of verbenone on spruce.

3 Claims, No Drawings

METHOD FOR INHIBITING SPRUCE BARK BEETLES

TECHNICAL FILED

The present invention relates to a method for inhibiting the six toothed spruce bark beetle, *Pityogenes chalcographus*.

The object of the present invention is to inhibit the infestation of the six toothed spruce bark beetle.

BACKGROUND OF THE INVENTION

The interest for biological methods for inhibiting pest insects has steadily increased during the last decade. This is particularly due for pheromones, the specie specific signal substances which some animals, in particular insects, communicate with, inter alia to find a partner prior to mating. Pheromone based inhibiting methods against pest insects are characterized in that 1) they are highly species specific, 2) the chemical compounds used are relatively simple, and biologically active in very small amounts to the target organism, often nanogram amounts, and 3) the insects have great difficulty in developing resistance against these natural signal compounds.

The high species specificity of the pheromones means that pheromone based inhibiting agents are directed almost only against individuals of one single species. Sometimes, furthermore, against closely related species. The chemical composition of the pheromones is as a rule of such a type that they will quite easily decompose by UV-light and microorganisms after an application. Then they are decomposed to compounds which are completely harmless to other organisms. This is natural as the pheromones as a behavior signal shall be short lived. They are thus not accumulated in higher organisms in a nutritional chain. The development of resistance in the insects against species specific pheromones is extremely improbable. In spite of a considerable use of, pheromones in the inhibition of e.g., a cotton fly in California for a whole decade, no resistance has developed. No change whatsoever in the composition of the pheromone has been demonstrated.

For the reason given above pheromone based inhibiting methods against pest insects are particularly harmless to the environment. Furthermore, they have proven to be extremely efficient.

Inhibition of forest damaging insects is an area where pheromone based inhibiting methods already are of great importance and have great economic value is at stake. This is particularly true for bark beetles which every year causes great losses both in the form of killed trees, growth losses and other damage, e.g., blueing fungus.

The six toothed spruce bark beetle, *Pityogenes chacographus* is one of the most serious forest pest insects in Europe. It can under certain circumstances attack and kill standing healthy spruces to a great extent.

The specie normally mates in healthy as well as in dying trees, e.g., wind fallen trees. The larvae live off the nutritionally rich bast layer (phloem) underneath the outer bark. A male that bores into that excretes a pheromone consisting of 2-ethyl-1,6-dioxaspiro-|4,4|-nonane, having the trivial name chalcogran (CH) and methyl-2,4-decadienoate (MD). Both substances are used commercially today as attractants. In the case of chalcogran, it is referred to in U.S. Pat. No. 4,205,084, and in the case of methyl decadienoate it is referred to in the Swedish Patent Application SE-A-8600448-8. Of chalcogran the 2S,5R-enantiomer is preferred, and of methyl ester the 2E,4Z isomer is preferred. The pheromone attracts females to the tree but also other males. The pheromone is well known and is utilized since it has long been used on a commercial scale as an attraction agent in traps for catching the six toothed spruce bark beetle.

The amount of pheromone excreted by an inbored male increases during the first days and thereby further males and females of the specie are attracted. By attracting further males he will obtain help in breaking down the defense system of the tree present in the form of a rich resin gum flow. The male will then gnaw out a mating chamber and is ready to allow one or more females therein, which after mating will start laying eggs therein. The amount of pheromone attraction agent then deceases and is down to a very low level about one week after the male has started his boring into the bark. This means that when many spruce bark beetles attack a tree then the attracting pheromone signal from the tree will increase rapidly. More bark beetles will be attracted and the number increases exponentially. Such a massive attack on a certain tree is characteristic for the reproduction strategy of the bark beetles. Certainly, it is, however, devastating if too many bark beetles are attracted to the same tree. The competition for the limited feed for the larvae will then become so great that many of them die. Thus the bark beetles excrete a stop signal for further attraction to that tree.

Usually, the six toothed spruce bark beetle lives in low population densities. In this endemic phase it mates in wind fallen, broken or otherwise damaged trees, which show a low vitality. Severe autumn storms which result in many wing fallen spruce offers, however, an excess of mating trees to the spruce bark beetle. The population thereof increases rapidly, and in particular if two such years follow on each other the spruce bark beetle can reach an epidemic phase in which the population density is so high that it, with success, can attack and kill also healthy spruces. Cut, unbarked spruce, which is left in the forest during the swarming of the spruce bark beetle in May to June is, from the insects point of view, a perfect mating place. In order to prevent the build up of epidemic population densities then piles of cut spruce have to be protected in some way. Today this is done in Sweden through legislation requiring cut spruce to be transported out of the forest before August 1, i.e., prior to the hatching of the new generation of spruce bark beetles.

DESCRIPTION OF THE PRESENT INVENTION

It has now surprisingly been shown possible to be able to prevent attraction and thereby attach on spruce by utilizing an inhibitor or stop signal compound of the pheromone related attraction by applying an inhibiting amount of (+) and/or (−)-verbenone, suitably in combination with an inert carrier.

The eight toothed and six toothed spruce bark beetles compete with one another for the spruce as a mating place. It is, as mentioned above, known through previous work, that verbenone is a stop signal of the eight toothed spruce bark beetle, whereby verbenone prevents attraction of further spruce bark beetles to its attracting agent.

The present invention will now be described more in detail with reference to the following examples, however, without being restricted thereto.

EXAMPLE

The inhibiting effect of verbenone on the six toothed spruce bark beetle against its attraction agent consisting of CH and MD was investigated in a field test. Hereby two glue traps were placed 1.7 m above the ends of a beam being 6 m long, which beam was rotated with a speed of 1 rpm/26 min. The traps consisted of a net cylinder having a diameter of 30 cm and having a height of 30 cm and manufactured of a net having a mesh size of 0.5 mm and being coated with Sticklem Special. The slow rotation of the pair of traps is intended to reduce the position caused variation of the trap catches which is common in field tests.

In a control test the two traps released the same amount or dose of E,Z-methyl decadienoate (18 μg/24 hrs) and chalcogran (1 mg/24 hrs) which is the aggregation pheromone of *Pityogenes chalcographus*. The catch did not significantly differ between the two traps. One trap caught 400 females and the other 422 females. Of the males 139, and 160 respectively, were caught.

At a completely similar distribution 411 females were caught in each trap, which using the $X^2$-test is not significantly different from 400/422 ($p=0.59$). The corresponding value for the males is $p=0.39$.

When the same test was repeated using the same attractants but with one of the traps furthermore provided with a verbenone dispenser releasing $9\times10^{-7}$ g per minute the catches were significantly reduced as evident from the Table 1 below.

| Sex | Trap 1 | Trap 2 | $X^2$-test |
|---|---|---|---|
|  | MD + CH | MD + CH |  |
| Females | 400 | 422 | p = 0.59 |
| Males | 139 | 160 | p = 0.39 |
|  | MD + CH | MD + CH +Vn |  |
| Females | 409 | 174 | p = <0.001 |
| Males | 165 | 100 | p = <0.001 |

In the test above $9.1\times10^{-7}$ g of verbenone were administered per minute. The active amount of verbenone can, however, be from $2.5\times10^{-9}$ g/min, preferably from $2.5\times10^{-8}$ g/min and in particular from $2.5\times10^{-7}$ to $2.5\times10^{-6}$ g/min.

At the use of verbenone for this purpose, verbenone is applied in an absorbent, such as silica, zeolites, or porous polymers, such as polyethylene, polycarbamide, or dextrose derivatives, or is dispersed in an emulsion of a cellulose derivative, such as CMC, hydroxymethyl cellulose, other starch glues or gum forming polysaccharides, so that the compound is released with an even amount for a long time. The absorbent is sprayed over the store of wood in the forest. As the wood does not become attacked, the transport out of the forest can be spread during a longer time period and can be made during the autumn. In the same way, summer cutting can take place which means a more rational handling within forestry.

The present invention can be used on standing spruce, but also, of course, on, and preferably on, cut spruce wood as well as fallen trees.

We claim:

1. A method for inhibiting the six toothed spruce bark beetle *Pityogenes chalcographus* by preventing the aggregation and/or infestation of the six toothed spruce bark beetle on spruce trees, said method comprising applying an effective amount of (+) and/or (−)-verbenone on spruce trees to inhibit the six toothed spruce bark beetle *Pityogenes chalcographus*.

2. The method according to claim 1, wherein said verbenone is applied such that verbenone is released at a rate of at least about $9\times10^{-7}$ g per minute.

3. The method according to claim 2, wherein said verbenone is applied such that verbenone is released at a rate of at least about $9\times10^{-6}$ g per minute.

* * * * *